United States Patent [19]
Saadat et al.

[11] Patent Number: 5,989,242
[45] Date of Patent: Nov. 23, 1999

[54] THERAPEUTIC APPLIANCE RELEASING DEVICE

[75] Inventors: Vahid Saadat, Sunnyvale; Samuel M. Shaolian, Laguna Niguel; Jeffrey J. Giba, Moreno Valley; Hung H. Cao, Corona; Randall Blair, Oceanside, all of Calif.

[73] Assignee: Trimedyne, Inc., Irvine, Calif.

[21] Appl. No.: 08/894,422

[22] PCT Filed: Jun. 26, 1996

[86] PCT No.: PCT/US96/11031

§ 371 Date: Aug. 19, 1997

§ 102(e) Date: Aug. 19, 1997

[87] PCT Pub. No.: WO97/01368

PCT Pub. Date: Jan. 16, 1997

Related U.S. Application Data

[63] Continuation-in-part of application No. 08/494,382, Jun. 26, 1995, abandoned.

[51] Int. Cl.[6] .................................................. A61B 17/00
[52] U.S. Cl. .................................................. 606/1; 606/151
[58] Field of Search ....................... 606/1, 108, 191–200, 606/151, 78; 623/1, 11, 12

[56] References Cited

U.S. PATENT DOCUMENTS

| | | | |
|---|---|---|---|
| 3,868,956 | 3/1975 | Alfidi et al. | |
| 4,035,007 | 7/1977 | Harrison et al. | 285/381 |
| 4,341,218 | 7/1982 | Ü. | |
| 4,512,338 | 4/1985 | Balko et al. | |
| 4,735,201 | 4/1988 | O'Reilly. | |
| 4,994,069 | 2/1991 | Ritchart et al. | 606/191 |
| 5,108,407 | 4/1992 | Geremia et al. | 606/108 |
| 5,133,721 | 7/1992 | Angulo | 606/106 |
| 5,167,624 | 12/1992 | Butler et al. | 604/60 |
| 5,217,484 | 6/1993 | Marks | 606/200 |
| 5,261,916 | 11/1993 | Engelson | 606/108 |
| 5,304,195 | 4/1994 | Twyford, Jr. et al. | 606/191 |
| 5,350,397 | 9/1994 | Palermo et al. | 606/108 |
| 5,354,295 | 10/1994 | Guglielmi et al. | 606/32 |
| 5,578,074 | 11/1996 | Mirigian | 623/1 |

*Primary Examiner*—Glenn K. Dawson
*Attorney, Agent, or Firm*—Olson & Hierl, Ltd.

[57] ABSTRACT

This invention is a device (10) for releasing a therapeutic appliance, such as an embolic coil (12) inside an aneurysm (16). The device includes a coupling (24) of a shape memory alloy which is responsive to a change in temperature beyond a predetermined transformation point so as to change the shape of the coupling from a first configuration, wherein the coupling receives and holds the proximal end (72) of the coil, to a second configuration wherein the coil can be released from the coupling. An energy receiver (46) is operably associated with the coupling to heat the coupling to a temperature above the transformation point with laser or electrical energy received from an external source.

15 Claims, 5 Drawing Sheets

THERAPEUTIC APPLIANCE RELEASING DEVICE

RELATED APPLICATIONS

This application is a continuation in part of U.S. patent application Ser. No. 08/494,382, filed on Jun. 26, 1995, now abandoned.

FIELD OF THE INVENTION

The present invention relates to a device for releasing a therapeutic appliance inside a patient and, more particularly, to a device for releasing an embolic coil at the site of an aneurysm.

BACKGROUND OF THE INVENTION

The recent growth of non-evasive surgical techniques has generated an increasing demand for devices capable of delivering a wide variety of therapeutic appliances to a specified location inside a patient's body. An embolic coil is one such therapeutic appliance which is released within an aneurysm pouch in a vessel or the like. The coil promotes the formation of a blood clot therein.

One such device for releasing an embolic coil within a vessel aneurysm is disclosed in U.S. Pat. No. 5,108,407 to Geremia et al. which includes a connector having a fiber optic receiving end and a embolic coil mounting end. Heat releasable adhesive bonds the coil to the mounting end of the connector. Laser energy transmitted through the fiber optic is converted to heat by the connector to cause the release of the adhesive bond between the connector and the coil and thus the release of the coil from the connector. With this device, there is the risk that melted adhesive may be deposited in a patient's bloodstream.

U.S. Pat. No. 5,261,916 to Engelson discloses a pusher-vasoocclusive coil assembly that is advanced through a catheter to a selected site within a vessel. The coil has an enlarged ball at its proximal end. The pusher has a keyway at its distal end that receives the ball in interlocking engagement. The pusher and coil are coupled by placing the ball in the keyway and enclosing the coupled assembly within a coaxial sleeve. The coil-pusher-sleeve assembly is positioned at the vessel site and the sleeve is retracted to allow the ball to move out of the keyway to release the pusher and coil.

U.S. Pat. No. 5,304,195 to Twyford, Jr. et al. discloses a pusher-vasoocclusive coil assembly including a coil carrying a ball on its proximal end and a pusher having a wire carrying a ball on its distal end. The pusher and coil are coupled by placing the balls in an overlapping interlocked position and enclosing the coupled assembly within a coaxial sleeve. The coil-pusher-sleeve assembly is then positioned at the site and the sleeve is retracted to allow the balls to move radially relative to one another to disengage and release the pusher and coil.

U.S. Pat. No. 5,354,295 to Guglielmi et al. discloses an embolic coil releasing device wherein a coil is soldered to a wire and separated therefrom at the vessel site either mechanically or by electrolytic separation.

U.S. Pat. No. 4,512,338 to Balko et al. discloses a device including a wire of shape memory alloy which is inserted into a vessel via a catheter while surrounded by insulation means. The insulation means is then removed and the wire expands into a coil configuration so as to occlude the vessel site.

U.S. Pat. No. 4,994,069 to Ritchart et al. discloses a device including a wire having a stretched, linear shape while being advanced through a catheter to a selected vessel and a helical coil shape when released from the catheter.

Despite the above prior art devices, improvements in efficiency and safety are still being sought. The present invention provides an improved therapeutic appliance releasing device which is efficient and safe to use.

SUMMARY OF THE INVENTION

A therapeutic appliance releasing device of the present invention provides for simple, safe and efficient delivery and release of a therapeutic appliance inside a patient's body.

The contemplated device for releasing a therapeutic appliance inside a patient's body includes a coupling comprised of a shape memory alloy which is responsive to a change in temperature beyond a predetermined transformation point so as to change its shape from a first configuration to a second configuration. The coupling is adapted to receive and hold a proximal end of the therapeutic appliance when in the first configuration and releasing the therapeutic appliance when in the second configuration. The coupling is operably connected to an external energy source. Further, an energy receiver is operably associated with the coupling to heat the coupling to a temperature above the transformation point with the energy received from the external source.

The coupling can include a pair of spaced-apart fingers of shape memory alloy which are responsive to a change in temperature beyond the predetermined transformation point so as to change their shape from a first configuration wherein the fingers are bent towards each other to hold the proximal end of the therapeutic appliance and a second configuration wherein the fingers are generally parallel to each other to release the proximal end of the therapeutic appliance.

In one embodiment of the present invention, the therapeutic appliance comprises an embolic coil adapted to be released within an aneurysm. The coil has a ball connected to a proximal end thereof. In this embodiment, the fingers hold the ball and the proximal end of the embolic when the fingers are in their first configuration and release the ball and the embolic coil when the fingers are in their second configuration.

The energy receiver comprises a wall operably associated and unitary with the coupling which receives and converts energy received from the energy source into heat transferable to the fingers to heat the fingers from about body temperature to a temperature of at least about 45 degrees C. so as to change the shape of the fingers from their first configuration to their second configuration.

The energy source can be a laser source which directs a laser beam through a fiber optic within the coupling and into the energy receiving wall or an electrical energy source.

Numerous other advantages and features of the present invention will become readily apparent from the following detailed description of the invention and the embodiments thereof, from the claims and from the accompanying drawings in which details of the invention are fully and completely disclosed as part of this specification.

DESCRIPTION OF THE PREFERRED EMBODIMENTS

The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

For ease of description, the therapeutic appliance releasing device embodying the present invention is described hereinbelow in its usual assembled position as shown in the accompanying drawings and terms such as upper, lower, horizontal, etc., will be used herein with reference to this usual position.

Some of the figures illustrating the therapeutic appliance releasing device of this invention show structural details and mechanical elements that will be recognized by one skilled in the art. However, the detailed descriptions of such elements are not necessary to an understanding of the invention, and accordingly, are not herein presented.

Additionally, the therapeutic appliance releasing device of this invention can be used with certain conventional components such as lasers, laser connectors, optic fibers, power supplies, resistors, transistors, shape memory alloys, and the like, the details of which, although not fully illustrated or described, will be apparent to those having skill in the art and an understanding of the necessary functions and structure of such components.

Figure 1:
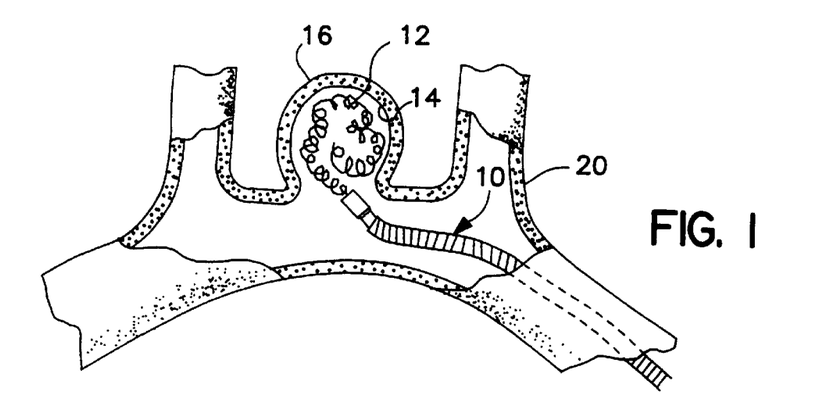
FIG. 1 is a schematic illustration of an intracranial aneurysm in the anterior communicating artery having an embolic coil positioned within the aneurysm prior to release.

FIG. 1 depicts a therapeutic appliance releasing device 10 according to the present invention and, more specifically, an embolic coil releasing device being used to position an embolic coil 12 within the pouch 14 of an intracranial aneurysm 16 in the anterior communicating artery 20. Although the Figures depict the use of the device 10 to release an embolic coil at the site of an aneurysm, it is understood that the device 10 may likewise be used to deliver and release any other type of desired therapeutic appliance within a patient's body.

Figure 2:
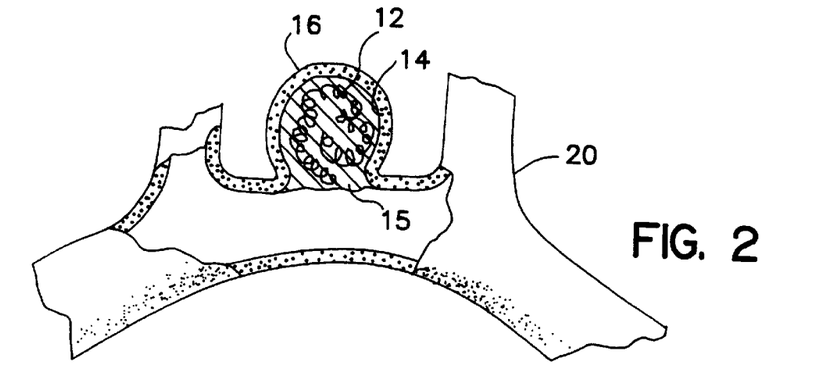
FIG. 2 is a schematic illustration of the same aneurysm showing the embolic coil released from the coupling and the aneurysm site repaired with a blood clot.

FIG. 2 depicts the embolic coil 12 implanted in the pouch 14 of the aneurysm 16 after the coil 12 has been released from the device 10 of FIG. 1. As is well known in the art, coil 12 provides a solid structure about which blood circulating in the aneurysm pouch 14 will congeal to form a clot 15.

Figure 3:
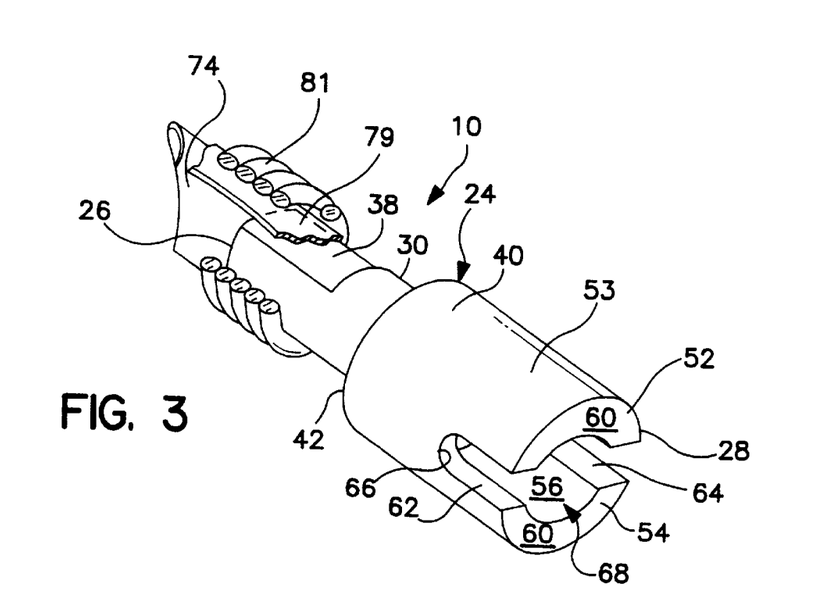
FIG. 3 is a perspective view of one embodiment of a shape memory alloy coupling of this invention.
Figure 4:
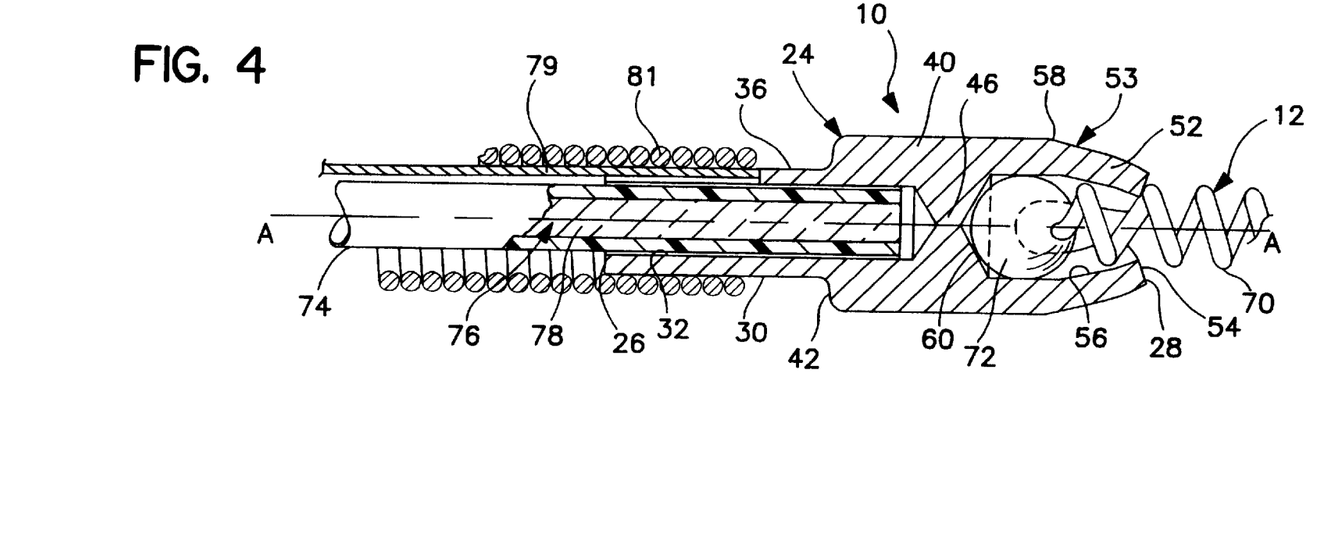
FIG. 4 is a side elevational view of the coupling, partly in section, and showing one end of an embolic coil held by the coupling.
Figure 5:
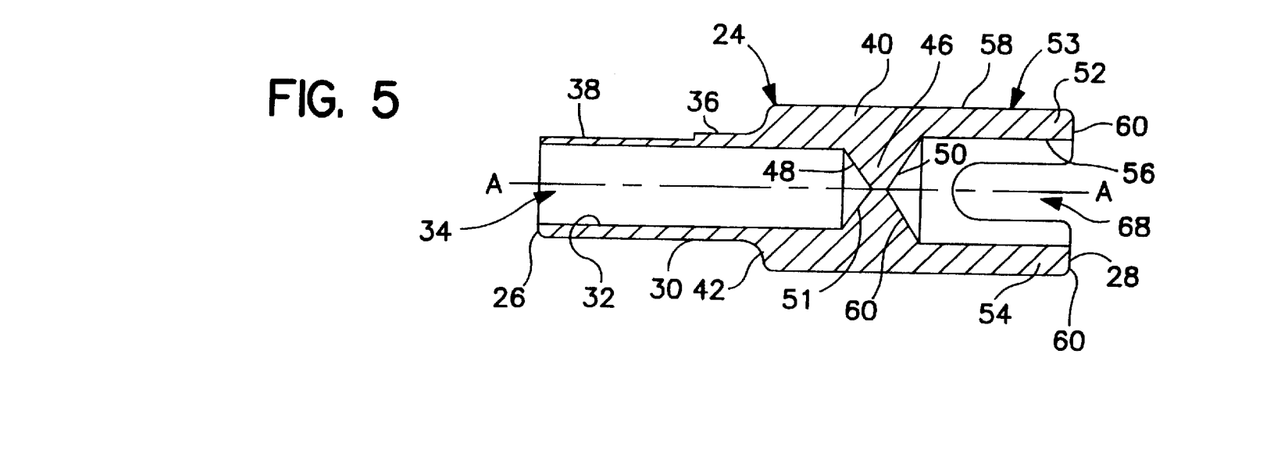
FIG. 5 is a side cross-sectional view of the coupling of the therapeutic appliance releasing device of the present invention with the end of the embolic coil released therefrom.

Referring to FIGS. 3–6, the device 10 includes a generally cylindrical housing or coupling 24 having a longitudinal axis A, a proximal end 26 and a distal end 28. Coupling 24 includes a generally cylindrical elongate neck 30 extending along the longitudinal axis A having an inner cylindrical elongate surface 32 defining a central hollow elongate cylindrical receptacle 34 (FIG. 5). Neck 30 also includes a generally cylindrical outer surface 36 with a flat land 38 thereon and extending a selected distance from the proximal end 26 of coupling 24 toward distal end 28 (FIG. 5).

Coupling 24 further includes a generally cylindrical body 40 having a diameter greater than the diameter of neck 30 and is joined thereto at radial shoulder 42 therebetween. Body 40 includes an interior wall 46, positioned between the ends 26 and 28 of coupling 24 and unitary with body 40. Wall 46 extends radially outwardly from and transverse to the longitudinal axis A of coupling 24 and serves as an energy receiver for energy supplied from an external source.

Referring to FIG. 5, wall 46 has opposite sides 48 and 50. Side 50 defines, in part, a receptacle or socket for the therapeutic appliance, while side 48 defines an energy receiver.

Figures 6, 7:
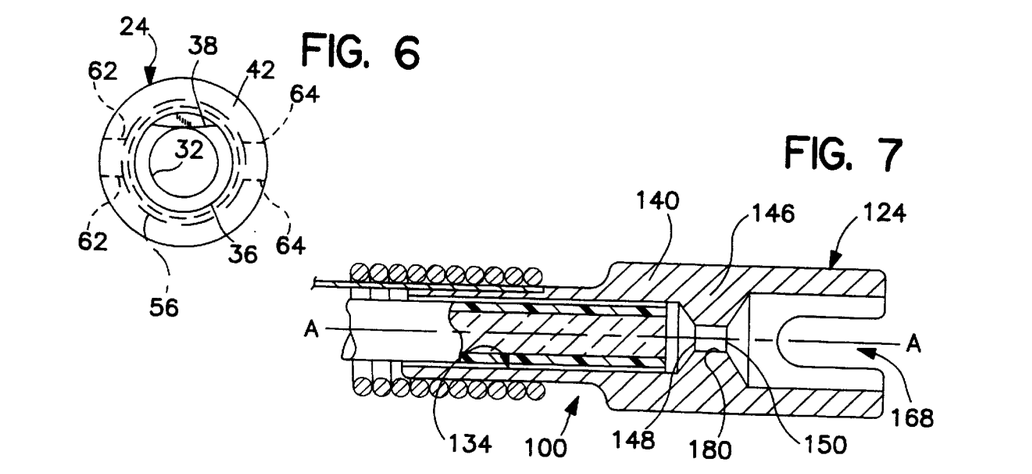
FIG. 6 is an end elevational view of the coupling of the therapeutic appliance releasing device depicted in FIG. 5.
FIG. 7 is a side elevational view, partly in section, of an alternate embodiment of the coupling and provided with an aperture in the central wall thereof.

In an alternate embodiment of the therapeutic appliance releasing device 100 as shown in FIG. 7.

Referring back to FIG. 5, the inner cylindrical surface 32 in the neck 30, and the receptacle 34 defined thereby, extends longitudinally into the interior of the body 40 centrally along the longitudinal axis A of coupling 24 and terminates in a cone-shaped surface 51 on side 48 of wall 46.

The coupling 24 further includes a grip 53 comprising a pair of spaced apart diametrically opposed elongate fingers 52 and 54 that extend generally away from the periphery of body 40 and, more particularly, from the periphery of the side 50 of wall 46. Each of the fingers 52 and 54 is in the shape of a cylinder segment with inner and outer cylindrical surfaces 56 and 58 respectively, an annular end face 60, and flat, longitudinally extending side faces 62 and 64. The side faces 62 and 64 of fingers 52 and 54 respectively are spaced from and face each other and are connected to each other by a curved shoulder 66 (FIG. 3).

The inner cylindrical surface 56 of fingers 52 and 54 defines a hollow generally cylindrical receptacle or socket 68 between the fingers 52 and 54 which extends inwardly into the coupling 24 centrally along the longitudinal axis A thereof. The inner cylindrical surface 56 terminates in a cone shaped surface 60 extending inwardly into the side 50 of wall 46.

The coupling 24 and, more particularly, the fingers 52 and 54 thereof, are made of a shape memory alloy such as a nickel-titanium alloy, e.g., NITINOL™, which is capable of maintaining a first configuration at a particular temperature and changing its shape to a second "memory" configuration when the alloy is heated beyond a predetermined transformation point or temperature. The term "shape memory alloy" as used herein refers not only to a nickel-titanium alloy but to any other material which exhibits shape memory characteristics.

In the preferred embodiment of the present invention, the fingers 52 and 54 are responsive to a change in temperature from a temperature of about body temperature to an elevated temperature, beyond a particular transformation temperature, of at least about 45 degrees C. so as to change the shape thereof from a first configuration wherein the fingers 52 and 54 are slightly bent towards each other (FIG. 4) to a second configuration (FIG. 5) wherein the fingers 52 and 54 are positioned generally parallel to each other and the longitudinal axis A of coupling 24.

As shown in FIG. 4, the fingers 52 and 54, when in their first configuration, are adapted to receive and hold the proximal end 70 of an embolic coil 12. As shown therein, coil 12 includes a ball 72, connected to the proximal end 70 thereof, which is received in the socket 68 between fingers 52 and 54 such that the outer surface of ball 72 abuts the inner cylindrical surface 56 and cone shaped radial surface 60 of fingers 52 and 54. The proximal end 70 of coil 12 is received in the socket 68 such that the outer surface thereof abuts the inner cylindrical surface 56 of fingers 52 and 54.

According to an alternate embodiment 100 of the present invention (FIG. 7), aperture 180 provides access to the embolic coil 12 in socket 168 from the receptacle 134. In this manner, the presence or absence of the therapeutic appliance in socket 168 can be ascertained by a feedback system that utilizes reflectometry if energy is supplied to the coupling from a radiant energy source such as a laser source by means of a fiber optic. Aperture 180 can also serve to provide a hydraulic assist means to expel the therapeutic appliance from socket 168 if energy is supplied from a hot water source via a tube, e.g, hot isotomic saline solution.

The coil 12 can be a fibered platinum coil commercially available from Target Therapeutics, Freemont, Calif., U.S.A. Typically, the embolic coil has an unrestrained diameter of the order of about 22 mm and a primary coil length of about 100 millimeters. The coil may be filled with DACRON® or other fibrous material to promote clotting, as is well known in the art. The embolic coil may be of any type known in the art to be suitable for the embolization of vascular aneurysms.

The ball 72 and proximal end 70 of coil 12 are released from the coupling 24 when the fingers 52 and 54 are positioned in their second parallel configuration as shown in FIG. 5. To assure a smooth and easy release, the inner cylindrical surfaces 56 and 60 of fingers 52 and 54 may be provided with a hydrophobic coating having a relatively low coefficient of friction, such as, but not limited to, a fluorocarbon coating, e.g., a TEPLON® coating. Additionally, capacitive feedback means may be associated with the fingers 52 and 54 and, more particularly, the inner surface 56 thereof, to signal the release of the coil 12 from the coupling 24.

The device 10 further includes an energy supply conduit such as a fiber optic cable 74 having a fiber optic 76 encased in a sheath or cladding 78 (FIGS. 3 and 4). The fiber optic 76 may be made of any suitable material such as quartz and the cladding 78 is preferable made of silica, but other biocompatible materials as are known in the art may also be used.

A safety ribbon 79 and wire coil 81 surround the cable 76. The distal end of ribbon 79 and wire coil 81 are secured to the proximal end 26 of coupling 24. More particularly, the distal end of ribbon 79 is seated in the flat portion 38 of neck 30.

The elongate proximal end of fiber optic cable 74 extends centrally and longitudinally along axis A through the receptacle 34 in neck 38 and base 44 and is spaced from the side 48 of wall 46 therein. The proximal end of cable 74 is secured in receptacle 34 by a high temperature epoxy of the like. The distal end (not shown) of fiber optic cable 74 is connected to a radiant energy source (not shown), such as a Nd:YAG laser with an output wavelength of about 1.06 microns or a Holmium:YAG laser (2.1 microns) and output power of about 3 to 5 watts, which transmits a laser beam through the fiber optic 76 and the proximal end thereof and then generally normal to the wall 46.

The wall 46 acts as an energy receiver having energy absorption characteristics designed to convert a substantial portion of the incident laser energy transmitted by fiber optic 76 into heat transferable to the fingers 52 and 54 unitary therewith to elevate their temperature from about body temperature to a temperature above at least about 45 degrees C. and thus change the shape thereof from their first configuration (FIG. 4) to their second configuration (FIG. 5) as described above.

Although the energy source described herein is a laser source, the present invention encompasses the use of any type of convenient energy source which the wall 46 can absorb and transform into heat, including, but not limited to, an electrical energy source, a radio frequency generator source or a hot water supply source.

The therapeutic appliance releasing device 10 is used to release a coil 12 inside an aneurysm as follows. Initially, the device 10, with the fingers 52 and 54 in their first configuration holding the proximal end 72 of coil 12 in the socket 68 (FIG. 4), is inserted and navigated through a patient's vessels or arteries (not shown) to the site to be occluded such as the intracranial aneurysm 16 shown in FIG. 1. Once the device 10 has been properly positioned in the interior of the artery 20 adjacent the aneurysm 16, the laser energy source (not shown) is energized to transmit laser energy through fiber optic 76 and then into the side 40 of wall 46. The wall 46 converts the laser energy into heat which the wall transfers to the fingers 52 and 54 unitary therewith to cause the temperature of the fingers to be elevated from about body temperature to a temperature of at least about 45 degrees C. whereupon the fingers 52 and 54 open up and assume their second configuration as shown in FIG. 5 releasing coil 12 within the pouch 14 of aneurysm 16. The laser energy source (not shown) is then deenergized and the device 10 is navigated out of the patient's body.

Figure 8:
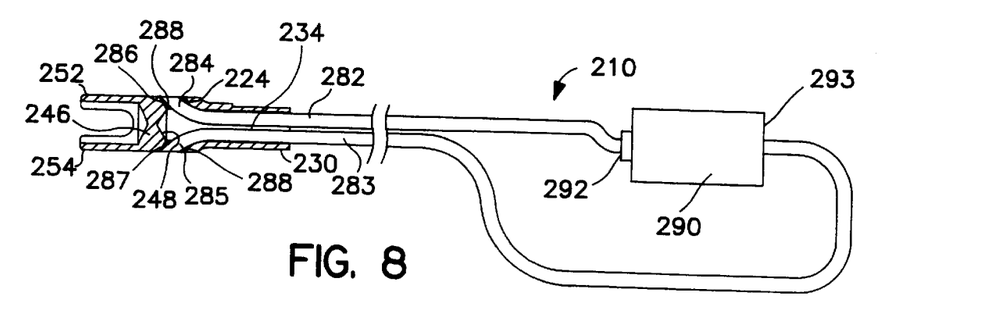
FIG. 8 is a schematic and a side elevation view, partly in section, illustrating another embodiment of a therapeutic appliance releasing device in accordance with the teachings of the present invention.

FIG. 8 depicts another embodiment of a therapeutic appliance releasing device of the present invention. The device 210 is similar to the devices described above except for the use of electrical energy to open fingers 252 and 254. Correspondingly, in the 200-series of numerals the last two digits depict structural elements that are similar in function to those described hereinabove and having numerals with the same last two digits.

In the device 210, two electrical leads 282 and 283 are used to direct electrical energy through wall 246. A substantial portion of the electrical energy flowing through the wall 246 is converted into heat which, in turn, is transferred to the fingers 252 and 254. The heat causes the fingers 252, 254 to separate from each other and thus release their grip on the coil or other therapeutic appliance disposed therebetween.

The electrical leads 282, 283 are preferably made of copper and extend within the neck 230 of the coupling 224. The electrical leads 282 and 283 have terminal end segments 284 and 285, respectively, which are received by two diametrical opposed oblique cylindrical open bores 286 and 287. The bores 286, 287 are in communication with the coupling receptacle 234 and are proximate to side 248 of wall 240. Each bore 286, 287 is associated with one of the fingers 252, 254 such that bore 286 is proximate to finger 252 and bore 287 is proximate to finger 254. Further, the bores 286, 287 slant towards the proximate end of their respective fingers 252, 254.

The terminal end segments 284, 285 of the leads are conductively attached to the coupling 224 by a conductive solder or epoxy 288 disposed within the bores 286, 287. The end segments 284, 285 and the epoxy 288 are flush with the cylindrically outer surface of the coupling 224 in order to provide the coupling with a smooth outer surface.

As shown in FIG. 8, the leads 282, 283 provide a means for operative connecting the coupling 324 to an external electrical energy source such as a conventional six (6) to nine (9) volt battery 290 having a voltage potential across terminals 292 and 293. An electrical current path is generated through wall 246 by connecting lead 282 to battery terminal 292 and lead 283 to battery terminal 293. The current which passes through the wall 246 of the conductive coupling 224 will generate heat and elevate the coupling temperature to about fifty (50) to sixty (60) degrees C. The heat is dissipated through the fingers 252 and 254. As the temperature of the fingers 252, 254 continues to increase, the fingers separate from each other and release their grip on the coil or other therapeutic appliance.

Figure 9:
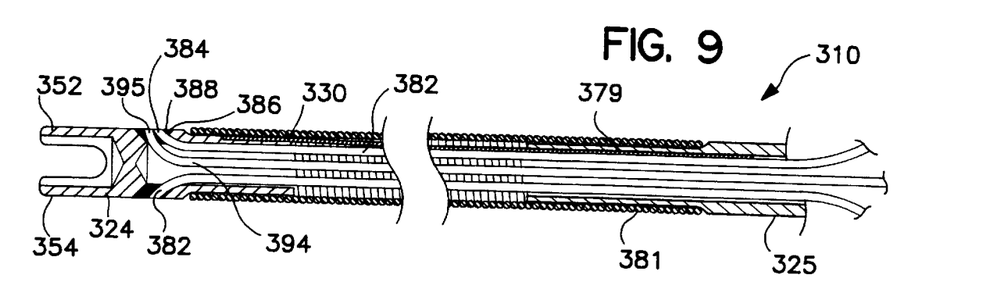
FIG. 9 is a side elevation view, partly in section, illustrating yet another therapeutic appliance releasing device in accordance with the present invention.

FIG. 9 depicts another therapeutic appliance releasing device 310 which is similar to that shown in FIG. 8 except for the addition of a feedback lead 394 which is used in determining whether the fingers 352, 354 are attached onto the embolic coil.

The feedback lead 394 extends within the neck 330 of the coupling 324 and is preferably made of copper. The terminal end 395 of the feedback lead 394 is received by bore 386. Both feedback lead terminal end 395 and electrical lead terminal end 384 are conductively connected to the coupling 324 by the conductive epoxy 388 within bore 386. Further, the end segments 395 and 384 preferably adjoin against each other and are flush with the cylindrically outer surface of the coupling 324.

Figure 10:
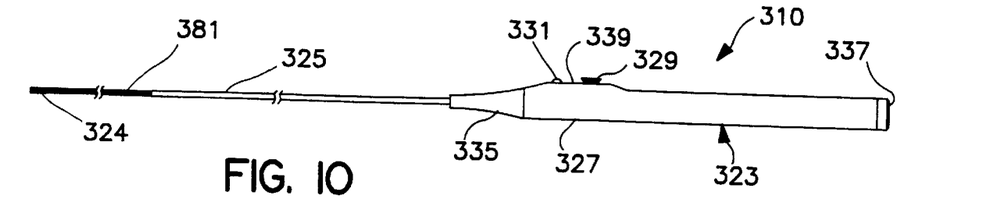
FIG. 10 is a side elevation view of a handle assembly having a button for releasing a therapeutic appliance and a display for indicating when the therapeutic appliance has been released.

The device 310 allows for determining if the embolic coil has been released from the coupling as explained in detail further herein and may include a handle assembly 323 as depicted in FIG. 10. The handle assembly 323 has a rigid hollow tube 325 fixedly attached at one end to safety ribbon 379 and wire coil 381. The 10 other end of the tube 325 is fixedly attached to a hard plastic or metal handle 327 having a thumb switch 329 for releasing the therapeutic appliance and a display 331 for indicating when the therapeutic appliance has been released.

Preferably, the handle 327 is generally tubular with a distally-tapered nose portion 335 and a proximal threaded end cap 337. The tube 325 of the device 310 longitudinally extends from the handle nose 335.

Further, the threaded cap 337 is removable from the handle to allow for inserting batteries within the tubular handle 327.

Protruding from handle 327 and proximate to the handle nose 335 is a substantially rectangular planar surface 339. The thumb switch 329 and the display 331 are positioned on the surface 339 such that the display is generally between the thumb switch 329 and the proximal end of the handle nose 335.

The thumb switch 329 is of conventional construction for connecting the electrical leads 382, 383 to the batteries within the handle 327. Correspondingly, depressing the thumb switch 329 will cause current to pass through the conductive coupling 324 and thus the separation of fingers 352 and 354.

Figure 11:
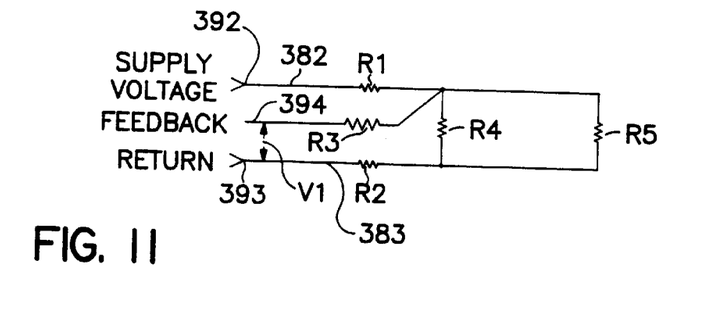
FIG. 11 is a detailed schematic of the electrical impedances while an embolic coil is held by the device depicted in FIGS. 9 and 10.
Figure 12:
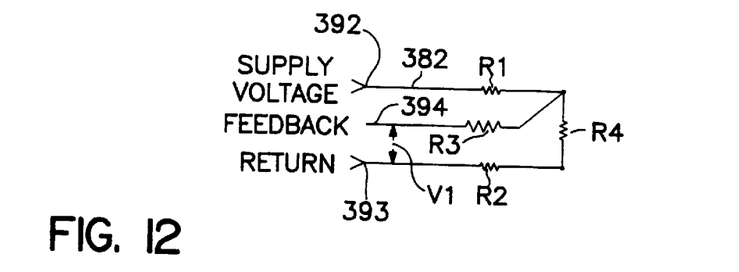
FIG. 12 is a schematic diagram of the electrical impedances once the embolic coil has been released from the device illustrated in FIGS. 9 and 10.

The display 331 is operative connected to electrical circuity within the handle 327 for detecting when the coil has been released by fingers 352 and 354. As illustrated by FIGS. 11 and 12, the operation of the circuitry which detects the release of the embolic coil is based on the electrical impedances of the device 310 while the coil is held, and then released, by fingers 352 and 354.

In FIG. 11, supply lead 382 and return lead 383 are connected to a generally stable supply voltage terminal 392 and return terminal 393, respectively. The supply lead 382 has a resistance of R1 and the return lead 382 has a resistance of R2.

As explained further herein, the feedback lead 394 is connected to the input of an operational amplifier wherein substantially no current from the supply voltage 392 passes through the resistance R3 of the feedback lead. This results in the current from the supply voltage 392 passing through R1, then in a parallel manner through the coupling having a resistance R4 and the coil ball having a resistance R5, and finally through R2. Therefore, the voltage potential V1 between the feedback lead 394 and the return terminal 393 generally consists of the voltage across R4 and R5, which are in parallel, plus the voltage across R2.

As depicted by FIG. 12, release of the ball from the coupling results in the removal of R5 as a source of resistance. Correspondingly, the voltage V1 between feedback lead 394 and return terminal 392 is reconfigured to consist of the voltage across R2 plus the voltage across R4. Thus, release of the coil ball results in an incremental increase in the voltage potential V1 due to the loss of the coil ball resistance R5.

Figure 13:
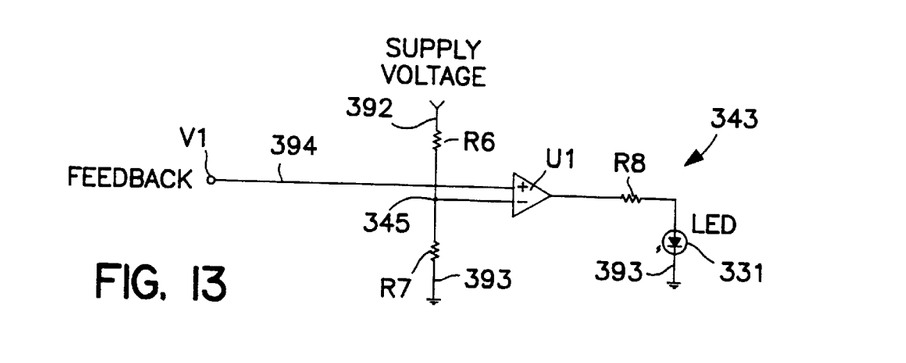
FIG. 13 is a detailed schematic circuit diagram of detection circuitry for determining if the embolic coil has been released from the device and for driving the display of FIG. 10 to indicate release of the coil.

The incremental increase in the feedback voltage V1 is detected by the circuitry 343 illustrated in FIG. 13. The detection circuitry 343 includes a conventional operational amplifier U1, such as a LM324 low power operational amplifier, wherein the noninverting input is connected to feedback lead 394 and a voltage reference 345 is applied to the inverting input. The voltage reference 345 is provided by connecting resistors R6 and R7 in series such that one end of resistor R7 is connected to return ground 393 and one end of resistor R6 is connected to the supply voltage 392.

The output of the operation amplifier U1 is connected to resistor R8. The other end of the resistor R8 is connected to the anode of the light emitting diode (LED) 331 which indicates the release of the coil ball. The cathode of the LED 331 is connected to return ground 393.

When the coil ball is attached to the fingers 352 and 354 of the device 310, the feedback voltage V1 provided at the non-inverting input of the operational amplifier U1 will be less than the voltage reference 345 connected to the inverting input of the operation amplifier U1. This will result in the output of the operation amplifier U1 being pulled to a "low" voltage level, thereby indicating that the coil ball is attached to the fingers by failing to illuminate LED 331.

Correspondingly, release of the coil ball from the fingers 352, 354 results in the feedback voltage V1 being incrementally increased to a voltage potential greater than that of the voltage reference 345. Thus, the output of the operational amplifier U1 will switch to a "high" voltage level to illuminate LED 331 which visually indicates the release of the coil ball from the fingers 352, 354 of the device 310.

Figure 14:
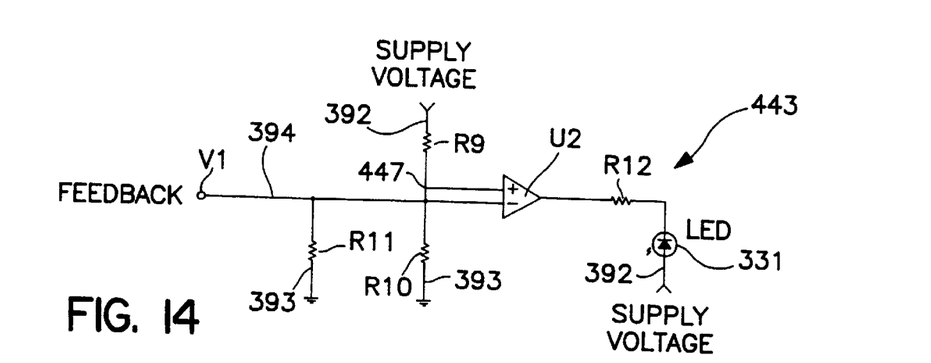
FIG. 14 is a schematic circuit diagram of another embodiment of detection circuitry for ascertaining when the coil has been released and for driving the display of FIG. 10 to indicated the occurrence of the release.

Another embodiment of detection circuitry 443 for ascertaining and indicating when the coil has been released is depicted by FIG. 14. The detection circuitry 443 includes a conventional operational amplifier U2 with the non-inverting input connected to a voltage reference 447 and the inverting input connected to feedback lead 394. The voltage reference 447 is provided by resistors R9 and R10 which are connected in series such that one end of resistor R10 is connected to the return ground 393 and one end of resistor R9 is connected to the supply voltage 392. Moreover, the feedback lead 394 is connected to resistor R11 which is tied to return ground 393.

The output of the operation amplifier U2 is attached to one end of a resistor R12. The other end of the resistor R12 is connected to the cathode of the display LED 331. The anode of the LED 331 is connected to the supply voltage 392.

In operation, the feedback voltage V1 provided at the inverting input of the operational amplifier U1 will be less than the voltage reference 447 connected to the non-inverting input when the coil ball is attached to the fingers 352 and 354 of the device 310. Thus, the output of the operation amplifier U1 is pulled to a "high" voltage level, thereby indicating that the coil ball is attached to the fingers by failing to illuminate LED 331.

Conversely, release of the coil ball from the fingers 352, 354 results in the feedback voltage V1 being incrementally increased to a voltage potential greater than that of the voltage reference 447. Thus, the output of the operational amplifier U1 will switch to a "low" voltage level to illuminate LED 331 which indicates the release of the coil ball from the fingers 352, 354 of the device 310.

Figure 15:
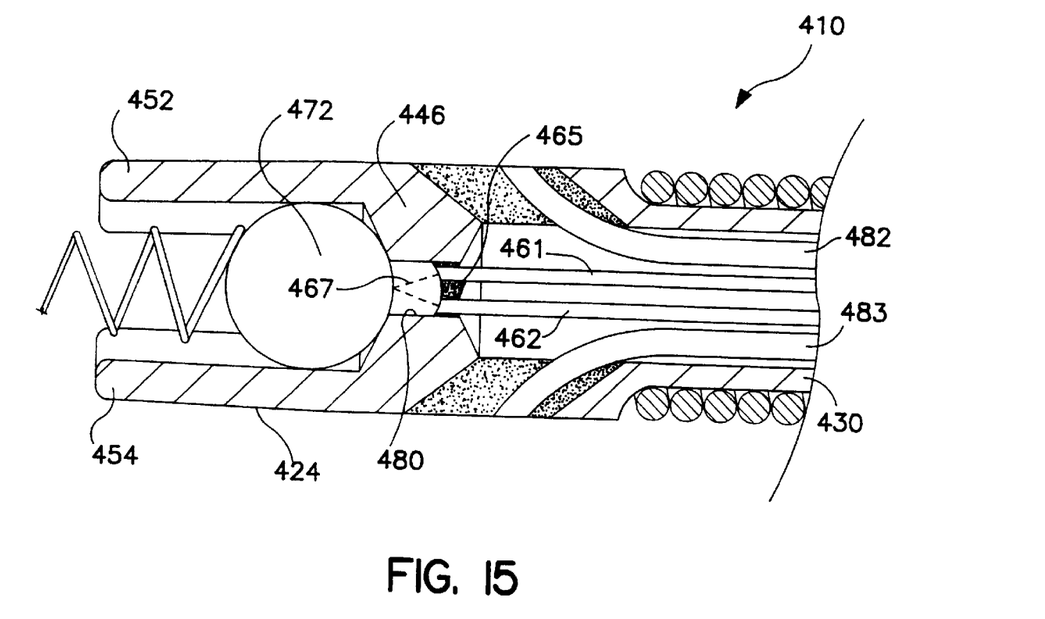
FIG. 15 is a side elevational view, partly in section, illustrating a further embodiment of a coupling holding onto an embolic coil.

FIG. 15 provides a side elevation view, partly in section, of yet another therapeutic appliance releasing device 410 in accordance with the present invention. The device 410 is similar to that shown in FIGS. 7–9 except for the use of reflectometry in determining whether the fingers 452, 454 are griping onto the coil ball 472. Correspondingly, in the 400-series of numerals the last two digits are the same as those similar structural elements described hereinabove.

The coupling 424 is provided with optical fibers 461, 463 partially extending into the cylindrical aperture 480 of the wall 446. Preferably, the optical fibers 461, 463 have a fifty (50) micrometer outer diameter with beveled distal ends.

The fibers 461, 463 extend within the neck 430 of the coupling 424 and are connected to the wall 446 by conventional epoxy 465. The distal end of the fibers 461, 463 are positioned within the aperture 480 such that light energy 467 emitted from fiber 461 will be reflected by the outer surface of ball 472 and received at the distal end of fiber 463.

Figure 16:
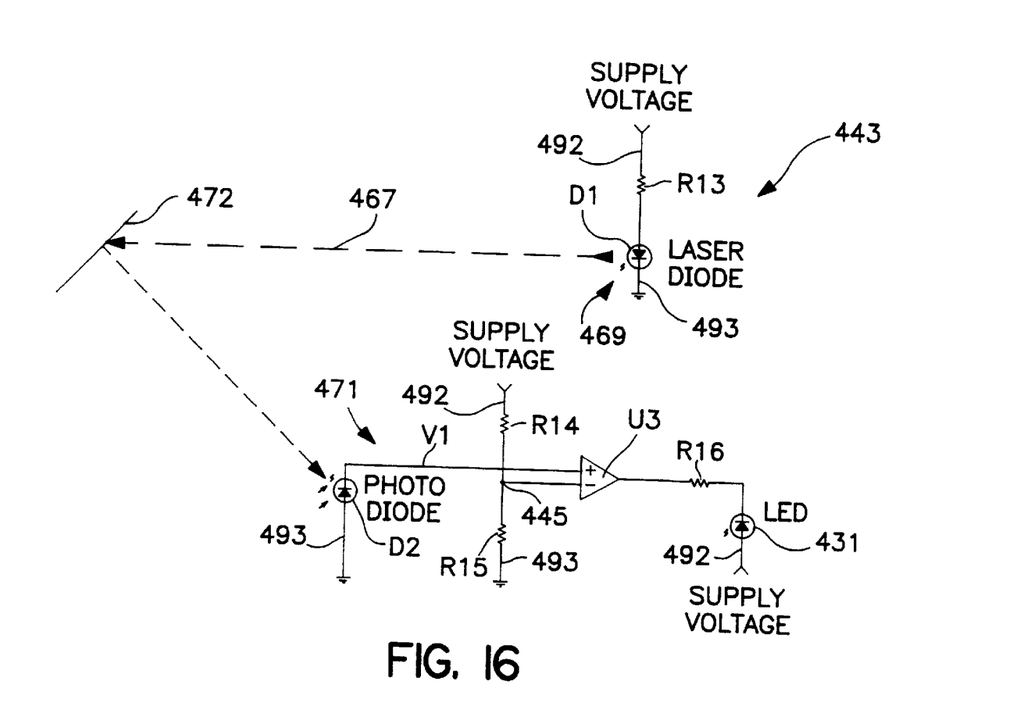
FIG. 16 is a schematic circuit diagram of another embodiment of detection circuitry for ascertaining and indicating when the coil of FIG. 15 has been released.

FIG. 16 illustrates detection circuitry 443 for using light energy 467 to ascertain the presence of the ball 472. The detection circuitry 443 includes laser energy generator 469 consisting of a convention laser diode D1 and a resistor R13. The resistor R13 is connected to the supply voltage 492 with the other end of the resistor connected to the anode of the diode D1. The cathode of the diode D1 is connected to return ground 493. The light energy 467 emitted by the laser diode D1 is received by optical fiber 461 and projects from the distal end of the fiber within the coupling aperture 480.

The detection circuitry also includes laser energy receiver circuitry 471 having a conventional operational amplifier U3 wherein the non-inverting input of the amplifier is connected to the cathode of a photo diode D2 and the inverting input is connected to a voltage reference 445. The voltage reference 445 consists of connecting resistors R14 and R15 in series such that one end of resistor R15 is connected to return ground 493 and one end of resistor R14 is connected to the supply voltage 492. Further, the anode of photo diode D2 is connected to return ground 493.

The output of the operation amplifier U3 is connected to one end of a resistor R16 with the other end of the resistor is connected to the cathode of the light emitting diode (LED) display 431. The anode of the LED 431 is connected to supply voltage 492.

When the coil ball 472 is attached to the fingers 452, 454 of the device 410, the light energy 467 emitted from the distal end of fiber 461 is reflected by the ball and received by fiber 462. The received light energy 467 is directed by fiber 462 onto photo diode D2 which results in the voltage V1 being provided at the non-inverting input of the operational amplifier U3. As the photo diode receives the light energy 467, the voltage V1 will be greater than that of the voltage reference 445 connected to the inverting input of the operation amplifier U3. Thus, the output of the operation amplifier U1 is pulled to a "high" voltage level, thereby indicating that the coil ball is attached to the fingers by failing to illuminate LED 431.

Correspondingly, release of the coil ball 472 from the fingers 452, 454 results in generally no laser energy 472 being received by photo diode D2. Thus, the feedback voltage V1 created by photo diode D2 will be incrementally decreased to a voltage potential less than that of the voltage reference 445. Therefore, the output of the operational amplifier U3 will switch to a "low" voltage level to illuminate LED 431 which indicates the release of the coil ball from the fingers 452, 454 of the device 410.

The device of the present invention thus provides a simple, safe, and efficient means by which a therapeutic appliance, such as an embolic coil, can be released inside a patient such as the site of an aneurysm.

Finally, it is understood that numerous variations and modifications of the embodiments described above may be effected without departing from the spirit and scope of the novel features of the invention. It is to be understood that no limitations with respect to the specific device illustrated herein are intended or should be inferred. It is, of course, intended to cover by the appended claims all such modifications as fall within the scope of the claims.

We claim:

1. A device suitable for releasing a therapeutic appliance inside a patient comprising:

a coupling of shape memory alloy responsive to a change in temperature beyond a predetermined transformation point so as to change its shape from a first configuration to a second configuration;

said coupling being adapted to receive and hold a proximal end of said therapeutic appliance when in said first configuration and releasing said therapeutic appliance when in said second configuration;

means for operably connecting an external energy source to said coupling;

an energy receiver connected to said coupling to heat said coupling to a temperature above said transformation point with energy received from said energy source; and means for detecting release of said therapeutic appliance from said coupling.

2. The device of claim 1 wherein said detecting means consists of electrical feedback detection circuitry operatively connected to said coupling.

3. The device of claim 2 wherein said detecting means includes an operational amplifier connected to a display for indicating release of said therapeutic appliance.

4. The device of claim 3 wherein said operational amplifier has a non-inverting input operatively connected to said coupling.

5. The device of claim 1 wherein said detecting means consists of optical feedback detection circuity operatively connected to said coupling.

6. The device of claim 4 wherein said detecting means includes an operation amplifier connected to a photo diode.

7. The device of claim 6 wherein said operational amplifier includes a non-inverting input connected to said photo diode.

8. The device of claim 1 wherein said coupling includes a pair of spaced-apart fingers of shape memory alloy and responsive to a change in temperature beyond a predetermined transformation point so as to change the shape of said fingers from a first configuration wherein said fingers are bent towards each other to hold said proximal end of said therapeutic appliance and a second configuration wherein said fingers are generally parallel to each other to release said proximal end of said therapeutic appliance.

9. The device of claim 1 wherein said energy source is a laser source.

10. The device of claim 1 wherein said energy source is an electrical energy source, and said energy receiver is operably connected to said coupling and the energy source.

11. An embolic coil releasing device which comprises an elongated housing having opposed ends and made of a shape memory alloy said housing having at one end a unitary grip for receiving and holding a proximal end of an embolic coil when at about body temperature and releasing said proximal end of said embolic coil when at a temperature of at least about 45 degrees C.; said housing defining at the other end a hollow receptacle that is unitary with said grip for receiving electrical leads capable of directing electrical energy through said receptacle for heating said housing and said grip to a temperature sufficient to release said embolic coil; and means for detecting release of said embolic coil from said housing.

12. The device of claim 11 wherein said detecting means consists of electrical feedback detection circuitry operatively connected to said housing and a light emitting diode display.

13. The device of claim 11 wherein said detecting means consists of optical feedback detection circuitry operably connected to said housing and a display.

14. An embolic coil releasing device in combination with an embolic coil comprising:

a generally cylindrical housing made of a shape memory alloy and elongated along a longitudinal axis;

a wall in the interior of said housing extending generally perpendicular to said longitudinal axis and including first and second sides;

a pair of elongated, spaced apart fingers extending away from and unitary with said first side of said wall, said fingers together defining an inner surface of a hollow generally cylindrical socket, said fingers being responsive to a change in temperature beyond a predetermined transformation point so as to change configuration from a first configuration wherein said fingers are bent towards each other and a second configuration wherein said fingers are generally parallel to each other and along said longitudinal axis of said housing;

said housing defining a second hollow receptacle adjacent said second side of said wall for receiving electrical leads capable of directing electrical energy through said wall for heating said wall and said fingers so as to change the shape of said fingers into said second configuration;

said embolic coil including a ball connected to the proximal end thereof, said socket defined by said fingers receiving and holding said ball and said proximal end of said embolic coil when said fingers are in said first configuration; said fingers releasing said ball and said embolic coil when said fingers are in said second configuration; and means for detecting release of said embolic coil from said fingers.

15. An embolic coil releasing device comprising:

a generally cylindrical housing made of a shape memory alloy and elongated along a longitudinal axis;

a wall in the interior of said housing extending generally perpendicular to said longitudinal axis and including first and second sides;

a pair of elongated spaced apart fingers extending away from and unitary with said first side of said wall, said fingers together defining an inner surface of a hollow generally cylindrical socket, said fingers being responsive to a change in temperature beyond a predetermined transformation point so as to change configuration from a first configuration wherein said fingers are bent towards each other and a second configuration wherein said fingers are generally parallel to each other and along said longitudinal axis of said housing;

said housing defining a second hollow receptacle adjacent said second side of said wall for receiving a fiber optic capable of directing a laser beam into said wall for heating said wall of said fingers so as to change the shape of said fingers into said second configuration;

said embolic coil including a ball connected to the proximal end thereof, said socket defined by said fingers receiving and holding said ball and said proximal end of said embolic coil when said fingers are in said first configuration; said fingers releasing said ball and said embolic coil when said fingers are in said second configuration and means for detecting release of said embolic coil from said fingers.

* * * * *